United States Patent
Acampora et al.

(10) Patent No.: US 6,537,286 B2
(45) Date of Patent: Mar. 25, 2003

(54) DEVICE FOR FASTENING A CRANIAL FLAP TO THE CRANIAL VAULT

(76) Inventors: Sergio Acampora, Via Francesco Petrarca 127, Naples (IT); Romolo Igino Gazzani, Piazza Matteotti 8, Serravalle Scrivia Alessandria (IT)

( * ) Notice: Subject to any disclaimer, the term of this patent is extended or adjusted under 35 U.S.C. 154(b) by 214 days.

(21) Appl. No.: 09/765,750

(22) Filed: Jan. 19, 2001

(65) Prior Publication Data

US 2002/0099395 A1 Jul. 25, 2002

(51) Int. Cl.[7] ............... A61B 17/08; A61B 17/56
(52) U.S. Cl. ............... 606/151; 606/72; 606/78
(58) Field of Search .................. 606/151, 157, 606/72, 78, 221; 411/82.5, 548, 909

(56) References Cited

U.S. PATENT DOCUMENTS

| | | | | |
|---|---|---|---|---|
| 3,586,002 A | * | 6/1971 | Wood | 606/221 |
| 5,474,557 A | | 12/1995 | Mai | |
| 5,549,620 A | * | 8/1996 | Bremer | 606/151 |
| 5,800,436 A | | 9/1998 | Lerch | |
| 6,068,631 A | * | 5/2000 | Lerch | 606/72 |
| 6,113,611 A | * | 9/2000 | Allen et al. | 606/151 |
| 6,171,320 B1 | * | 1/2001 | Monassevitch | 606/151 |
| 6,197,037 B1 | * | 3/2001 | Hair | 606/151 |
| 6,302,884 B1 | * | 10/2001 | Wellisz et al. | 606/69 |
| 6,402,765 B1 | * | 6/2002 | Mnassevitch et al. | 606/151 |

FOREIGN PATENT DOCUMENTS

| | | |
|---|---|---|
| DE | 19634697 | 4/1998 |
| EP | 0873718 A3 | 10/1998 |
| EP | 0873718 A2 | 10/1998 |
| WO | WO98 29040 | 7/1998 |

OTHER PUBLICATIONS

European Search Report—dated Jul. 17, 2001.

* cited by examiner

Primary Examiner—Rodney M. Lindsey
(74) Attorney, Agent, or Firm—Hedman & Costigan, P.C.

(57) ABSTRACT

A device (10) for fastening a cranial flap (17) to the cranial vault (16), comprising an upper ring (11) and a lower ring (12), connected to each other by a pillar (13), where the upper ring (11) is composed of two sections (18, 19) and may assume a first configuration in which the sections (18, 19) are approached, and a second configuration in which the sections (18, 19) are spread apart.

7 Claims, 3 Drawing Sheets

DEVICE FOR FASTENING A CRANIAL FLAP TO THE CRANIAL VAULT

Figure 1:
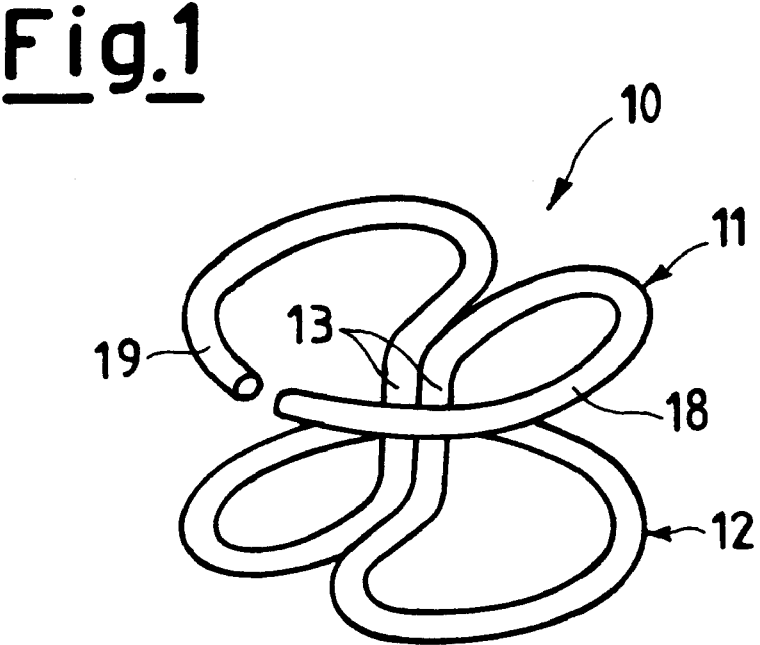

This invention refers to a device for fastening a cranial flap to the cranial vault.

As known, a craniotomy, meaning the incision and cutting out of a bone flap from the cranial vault, is a mandatory neurosurgical procedure for the treatment of any inter-cranial damage.

This procedure is generally carried out in the following manner: after properly positioning the patient depending on the intended action and planning the flap, the scalp is disinfected, the skin incising outline is drawn up and the head is covered with sterile linen.

The skin incision is performed in short sections, while controlling the hemostasis by bipolar coagulation and the application of skin clips.

After the incision has been completed, the flap of scalp is detached from the underlying pericranium, and the pericranium and muscle are incised by a diathermic cut along the intended bone flap outline, except for occasionally leaving a shaft to allow for a certain blood flow to the bone.

In certain flaps, especially those of a frontal or pterional type, the dissociation of these planes may be avoided, so as to spare the nerve endings of the facial nerve.

The bone flap is thereupon incised by drilling one or several holes, depending on whether a cutting blade or a drill bit on a pneumatic drill is applied, so that the underlying cranial vault may be detached free hand by the key hole while simultaneously incising the bone, or the hard part of the bone is dissected between one drill hole and the next by using a curved periosteum detacher. In the following, a sawing wire is guided through and pulled upward by hand at the extremities, thus excising the bone in individual segments.

The bone flap is wrapped in moist gauze and kept apart from the operating area by some fastening devices if provided with a shaft, or left free in a physiological solution in a cup.

At the end of the neurosurgical operation, after the cranial vault has been sutured and the bone edges have been turned up, the flap is refitted into the aperture and fastened with separate metal points or wires passed through small drill holes provided in pairs along the free edge of the cranial bone.

The cranial flap is occasionally left entirely free, except for a thread of silk applied on the cranial vault, passed through two drill holes and tied to the center of the bone flap.

It is nevertheless evident that solutions of this type cannot generally afford an esthetically acceptable seal, as they are not always capable of preventing the bone flap from emerging, curving, sloping or turning. In order to prevent these drawbacks, some micro-platelets made of titanium have more recently been applied by threading them in at three points on the bone flap and along the edge of the cranial vault.

Nevertheless, even this solution suffers from the fact that these micro-platelets made of titanium are not sufficiently elastic to ensure that an excess pressure will not arise on the brain during the post-operation period.

The purpose of this invention is therefore to produce a device for fastening a cranial flap to the cranial vault, capable of ensuring a correct ossification of the bone flap along the edge of the cranial vault. Another purpose of the invention is to produce a device for fastening a cranial flap to the cranial vault, capable of ensuring a lower pressure on the brain itself, even if a cerebral edema should develop during the post-operation period.

These and other purposes are achieved by a device for fastening a cranial flap to the cranial vault, according to claim 1, which is being referred to for brevity.

Other characteristics of the invention are defined in the additional claims attached to this patent application.

Figure 2:
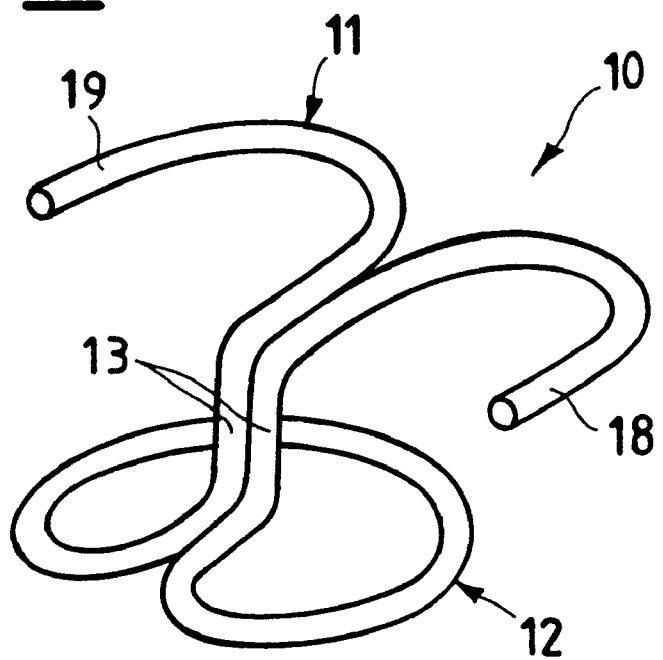
Figure 3:
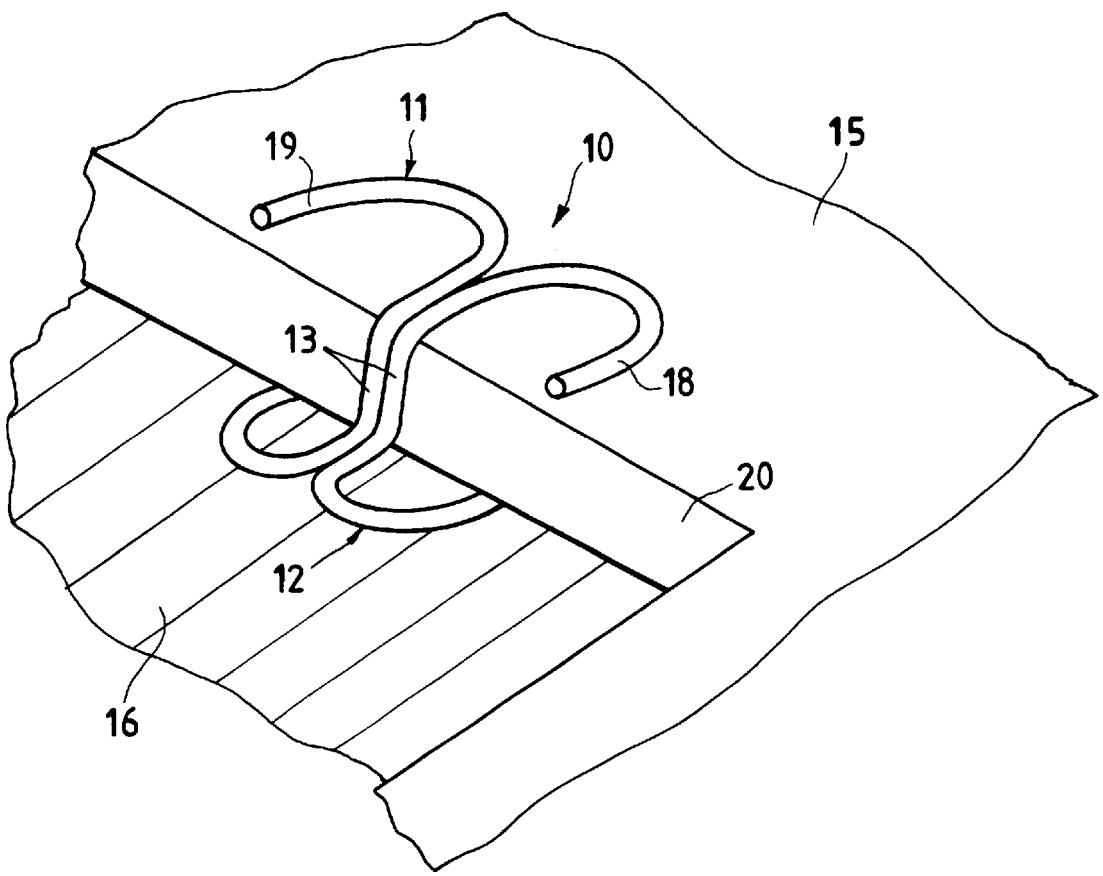
Figure 4:
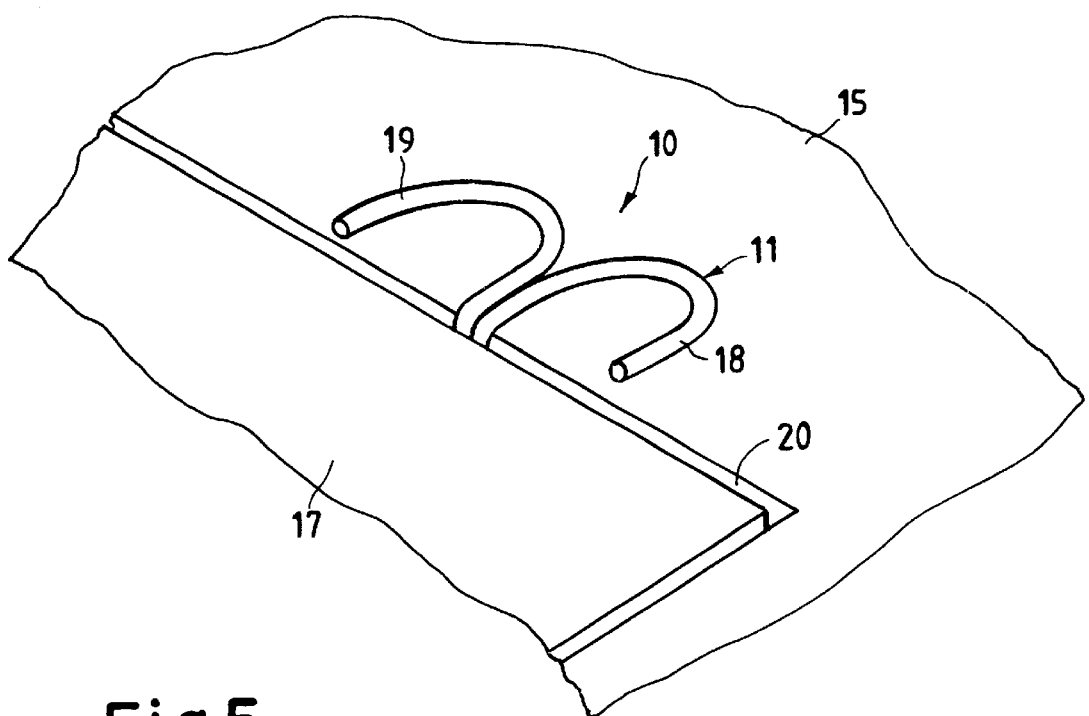
Figure 5:
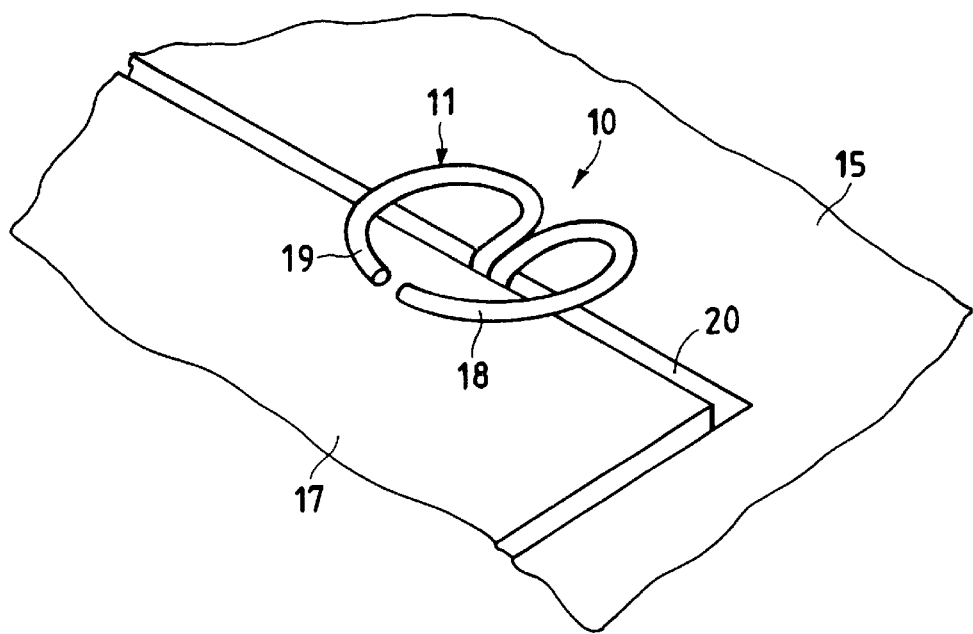

Further scopes and advantages of this invention will become clear from the description and attached drawings to follow, supplied for purely explanatory and non-limiting purposes, in which:

FIG. 1 shows a view of the device for fastening a cranial flap to the cranial vault, according to this invention, in a closed configuration, FIG. 2 shows a view of the device of FIG. 1, in an open configuration, FIG. 3 shows a view of the device of the invention in a first phase of its application, FIG. 4 shows a view of the device of the invention in a second phase of its application, and FIG. 5 shows a view of the device of the invention in a further phase of its application.

With particular reference to the figures mentioned above, the device for fastening a cranial flap to the cranial vault according to this invention is indicated in its overall form by reference to the number 10. The device 10 includes an upper ring 11 and a lower ring 12, connected to each other by a pillar 13.

The entire structure of the device 10 is made from a single wire; this particular design provides for an opened upper ring 11, composed in particular of two sections 18 and 19, and for a closed lower ring 12. Moreover, the fact that the structure of the device 10 is made from a single wire achieves a pillar 13 be constituted by two adjacent sections of wire.

The elasticity of the pillar 13 connecting the two rings 11 and 12 makes it possible to utilize only a few sizes in relation to the bone thickness 20, for example only three sizes, while its circular form allows any rotating motion, including a shifting of the rings out of a parallel plane.

The wire used to produce the device 10 is preferably made of a nickel-titanium alloy with a memorized form. Going into further detail in relation to the applications of the cranial fastening device 10 of this invention, it is worth noting that the instrument specialist sets up a number of devices 10 to handle a craniotomy in various sizes, by placing them into a small cup (not shown) containing a chilled physiological solution, for instance at a temperature of −8° C.

The instrument specialist grasps the upper ring 11 with a grooved clamping forceps and then laterally twists the sections 18 and 19 of the ring 11 by a knurled forceps, until opening them as shown in FIG. 2.

Using the clamping forceps, the surgeon then inserts the device 10 so that the pillar 13 comes in contact with the bone edge 20, while passing the lower ring 12 through the space between the bone 15 and the cranial vault 16.

These operations are carried out by choosing the sizes most suited to the thickness of the bone 15 and the most appropriate number of devices 10, in relation to the size and shape of the craniotomy, as shown in FIG. 3.

The bone operculum 17 is rested on the lower ring 12 of the device 10, as shown in FIG. 4.

The surgeon then verifies the proper position of the operculum 17, irrigates the devices 10 with a hot physiological solution (for example at a temperature of 45° C.), until the upper ring 11 is fully closed; this operation is shown in FIG. 5.

The cranial fastening device 10 of this invention is suitable for any craniotomy, as its shape and the various sizes in which it can be produced based on the bone thickness allow it to adhere to the cranial flap at the edge of the cranial vault, both at the inner and outer perimeter, so as to permit a proper ossification process.

The device 10 can be utilized to fasten a vole inserted into the cranial vault instead of for instance resorting to the use of micro-plates and screws.

At the same time, the extreme elasticity of the nickel-titanium alloy guarantees a lower pressure on the brain itself during the post-operation period, when edemas and therefore brain swelling phenomena may occur.

The above description clearly outlines the characteristics as well as the advantages of the device for fastening a cranial flap to the cranial vault as an object of this invention.

It is also evident that numerous variants may be applied to the device for fastening a cranial flap to the cranial vault, as an object of this invention, without thereby abandoning the principles of novelty inherent in the inventive idea.

Finally and in the practical implementation of the invention, the materials, shapes and sizes of the details outlined above may be of any kind depending on the requirements, and the same may be substituted by others of a technically equivalent type.

What is claimed is:

1. A device (10) for fastening a cranial flap (17) to the cranial vault (16), characterized in that it provides for an upper ring (11) and a lower ring (12) connected to each other by a pillar (13), where said upper ring (11) is composed of two detachable sections (18, 19) and may assume a first configuration in which the mentioned sections (18, 19) are approached, and a second configuration in which the mentioned sections (18, 19) are spread apart.

2. A device (10) according to claim 1, characterized in that said pillar (13) may be placed in contact with the bone edge (20), by passing the lower ring (11) through the space between the bone (15) and the cranial vault (16), so that a bone flap (17) may subsequently be rested on said lower ring (12).

3. A device (10) according to claim 2, characterized in that said sections (18, 19) of the upper ring (11) may be rotated laterally until opened, so as to allow the mentioned bone flap (17) to be rested on the same, and subsequently approached until the upper ring (11) is closed, so as to hold the mentioned bone flap (17), while irrigating them with a hot physiological solution.

4. A device (10) according to claim 1, characterized in that said lower ring (12) is closed.

5. A device (10) according to claim 1, characterized in that the entire structure of the device (10) is produced from a single wire in a material having a memorized shape.

6. A device (10) according to claim 5, characterized in that said pillar (13) is constituted of two sections of the same wire, set side by side.

7. A device (10) according to claim 6, characterized in that said wire is made of a nickel-titanium alloy.

* * * * *